United States Patent [19]

Matsumoto et al.

[11] Patent Number: 5,498,725
[45] Date of Patent: Mar. 12, 1996

[54] PROCESS FOR PREPARING 5-AMINODIHYDROPYRROLE INTERMEDIATE THEREOF AND PROCESS FOR PREPARING SAID INTERMEDIATE

[75] Inventors: Misuhiro Matsumoto, Osaka; Kunihiko Fujita, Aomori, both of Japan

[73] Assignee: Sumitomo Chemical Company, Limited, Osaka, Japan

[21] Appl. No.: 354,804

[22] Filed: Dec. 13, 1994

[30] Foreign Application Priority Data

Dec. 15, 1993 [JP] Japan ................... 5-315504
Dec. 15, 1993 [JP] Japan ................... 5-315505

[51] Int. Cl.$^6$ ................... C07D 207/32
[52] U.S. Cl. ............ 548/408; 548/542; 548/558
[58] Field of Search ................... 548/558, 408, 548/542

[56] References Cited

U.S. PATENT DOCUMENTS 4,016,175  4/1977  Schaafsma et al. ............ 548/408

FOREIGN PATENT DOCUMENTS 0406993  1/1991  European Pat. Off. .
0448188  9/1991  European Pat. Off. .
2542396  4/1976  Germany .
2163427  2/1986  United Kingdom .

OTHER PUBLICATIONS

Journal of Organic Chemistry, vol. 43, No. 16, 1978, pp. 3101–3107, F. G. Bordwell et al. *The Taft Equation As . . .*

Journal of the Chemical Society, 1947, pp. 1505–1508, G. D. Buckley et al. *Aliphatic Nitro-compounds . . . .*
J. Chem. Soc. Nitroxide Radicals . . . 1–Oxides. Forrester et al., pp. 1224–1231, 1965.

CA60:3616e The structure . . . N–oxide. Forrester et al., 1964.
CA62:9092g Nitroxide redicals . . . 1–oxides. Forrester et al., 1965.
CA86:29567b Synthesis . . . 2–phenylalkanenitriles. Jaw dosiuk et al., 1977.
CA88:74264c Synthesis . . . –indoles. Munshi et al., pp. 476, 1978.
CA116:194083m Cyclization . . . compounds. Nasakin et al., p. 704, 1992.
G. D. Buckley et al "Aliphatic Nitro–Compounds. Part XV. Preparation Of Heterocyclic Bases By Reduction Of 3–Nitroalkyl Cyanides." (1947), J. Chem. Soc.
"Monatsh. Chem." pp. 1263 (1970), (5), Klötzer et al.

*Primary Examiner*—Joseph K. McKane
*Attorney, Agent, or Firm*—Birch, Stewart, Kolasch & Birch

[57] ABSTRACT

A 5-aminodihydropyrrole of the formula (1):

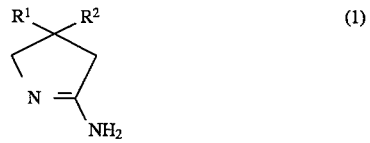

(1)

in which $R^1$ and $R^2$ independently represent a hydrogen atom, a lower alkyl group or a lower haloalkyl group, or together form a $C_2$–$C_{10}$ alkylene group optionally substituted with a halogen by reducing an oxidepyrrole of the formula (2):

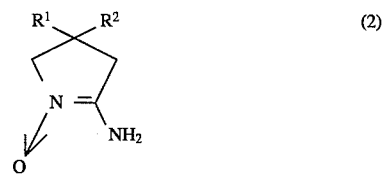

(2)

in which $R^1$ and $R^2$ are the same as defined above, with hydrogen in the presence of a catalyst.

16 Claims, No Drawings

PROCESS FOR PREPARING 5-AMINODIHYDROPYRROLE INTERMEDIATE THEREOF AND PROCESS FOR PREPARING SAID INTERMEDIATE

BACKGROUND OF THE INVENTION

1. Field of the Invention

The present invention relates to a process for preparing 5-aminodihydropyrrole which is useful as a raw material of agrochemicals, an oxidepyrrole which is a key intermediate for the preparation of 5-aminodihydropyrrole, and a process for preparing said intermediate.

2. Description of the Related Art

A 5-aminodihydropyrrole of the formula (1):

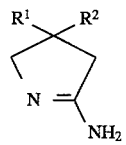

(1)

wherein $R^1$ and $R^2$ are the same or different and represent a hydrogen atom, a lower alkyl group or a lower haloalkyl group, or together form a $C_2$–$C_{10}$ alkylene group which may be substituted with a halogen is known to be useful as a raw material of agrochemicals such as benzoxadine or benzoxazoline type herbicides. But, its preparation process has not been known.

As a related process, there is known a process for preparing a 2-substituted-5-aminodihydropyrrole from a corresponding N-oxide compound using sodium and an alcohol, or distilling it in the presence of zinc, or using iron and hydrochloric acid (cf. *J. Chem. Soc.*, (1947) 1508). However, this process is unsatisfactory in the technical production, since sodium, zinc or iron should be used in a large amount and a yield of the desired compound is low.

There is also known a process for preparing 3-phenyl-5-aminodihydropyrrole by treating a 4-phenyl-2-pyrrolidone compound with phosphorus oxychloride and ammonia (cf. *Monatsh. Chem.*, 101 (5), 1970, 1263). However, this process cannot be used for the preparation of a 5-aminodihydropyrrole having no phenyl group at the 3-position such as the 5-aminodihydropyrrole of the formula (1), which is an important raw material of agrochemicals cannot be obtained by this method.

Accordingly, it is highly desired to find a process for preparing the 5-aminodihydropyrrole (1), in particular, which is excellent for industrial scale production.

SUMMARY OF THE INVENTION

One object of the present invention is to provide an industrially excellent process for preparing the 5-aminodihydropyrrole (1).

Another object of the present invention is to provide a compound which is a key intermediate in the preparation of the 5-aminodihydropyrrole (1).

According to a first aspect of the present invention, there is provided a process for preparing a 5-aminodihydropyrrole of the formula (1):

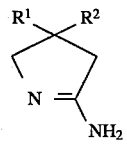

(1)

wherein $R^1$ and $R^2$ are the same or different and represent a hydrogen atom, a lower alkyl group or a lower haloalkyl group, or together form a $C_2$–$C_{10}$ alkylene group which may be substituted with a halogen comprising reducing an oxidepyrrole of the formula (2):

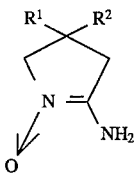

(2)

wherein $R^1$ and $R^2$ are the same as defined above with hydrogen in the presence of a catalyst.

According to a second aspect of the present invention, there is provided a process for preparing an oxidepyrrole of the formula (2) comprising reducing a 4-nitrobutanenitrile of the formula (3):

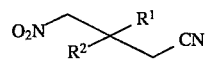

(3)

wherein $R^1$ and $R^2$ are the same as defined above with hydrogen in the presence of a catalyst.

According to a third aspect of the present invention, there is provided a process for preparing a 4-nitrobutanenitrile of the formula (3) comprising reacting an alkenylnitrile of the formula (4):

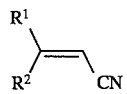

(4)

or the formula (4'):

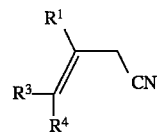

(4')

wherein $R^1$ and $R^2$ are the same as defined above and $R^3$ and $R^4$ are the same or different and represent a hydrogen atom, a $C_1$–$C_4$ alkyl group or a lower $C_1$–$C_4$ haloalkyl group with nitromethane in the presence of a base.

According to a fourth aspect of the present invention, there is provided an oxidepyrrole of the formula (2).

According to a fifth aspect of the present invention, there is provided a 4-nitrobutanenitrile of the formula (3).

DETAILED DESCRIPTION OF THE INVENTION

The present invention will be explained further in detail.

The lower alkyl or haloalkyl group for $R^1$ and $R^2$ has usually 1 to 5 carbon atoms and may be a straight or branched group. Examples of the lower alkyl group are a methyl group, an ethyl group, a propyl group, an isopropyl group, a butyl group, a sec.-butyl group, a tert.-butyl group, an amyl group, a tert.-amyl group, and the like. Example of the lower haloalkyl group are a fluoromethyl group, a difluoromethyl group, a trifluoromethyl group, a pentafluoroethyl group.

Alternatively, $R^1$ and $R^2$ together form a $C_2$–$C_{10}$ alkylene group which may be substituted with at least one halogen atom (e.g. a chlorine atom, a fluorine atom, a bromine atom, or an iodine atom).

Specific examples of the oxidepyrrole (2) are 5-amino-3,4-dihydro-1-oxide-2H-pyrrole, 5-amino-3,4-dihydro-3,3- dimethyl-1-oxide-2H-pyrrole, 5-amino-3,4-dihydro-3,3-diethyl-1-oxide-2H-pyrrole, 5-amino-3,4-dihydro-3,3-dipropyl-1-oxide-2H-pyrrole, 5-amino-3,4-dihydro-3,3-bis(fluoromethyl)-1-oxide-2H-pyrrole, 5-amino-3,4-dihydro-3,3-bis(difluoromethyl)-1-oxide-2H-pyrrole, 5-amino-3,4-dihydro-3,3-bis(trifluoromethyl)-1-oxide-2H-pyrrole, 5-amino-3,4-dihydro-3,3-bis(pentafluoroethyl)-1-oxide-2H-pyrrole, 5-amino-3,4-dihydro-3-methyl-1-oxide-2H-pyrrole, 5-amino-3,4-dihydro-3-ethyl-1-oxide-2H-pyrrole, 5-amino-3,4-dihydro-3-propyl-1-oxide-2H-pyrrole, 5-amino-3,4-dihydro-3-isopropyl-1-oxide-2H-pyrrole, 5-amino-3,4-dihydro-3-butyl-1-oxide-2H-pyrrole, 5-amino-3,4-dihydro-3-tert.-butyl-1-oxide-2H-pyrrole, 5-amino-3,4-dihydro-3-sec.-butyl-1-oxide-2H-pyrrole, 5-amino-3,4-dihydro-3-fluoromethyl-1-oxide-2H-pyrrole, 5-amino-3,4-dihydro-3-difluoromethyl-1-oxide-2H-pyrrole, 5-amino-3,4-dihydro-3-trifluoromethyl-1-oxide-2H-pyrrole, 5-amino-3,4-dihydro-3-pentafluoroethyl-1-oxide-2H-pyrrole, 5-amino-3,4-dihydro-3-ethyl-3-methyl-1-oxide-2H-pyrrole, 5-amino-3,4-dihydro-3-isopropyl-3-methyl-1-oxide-2H-pyrrole, 5-amino-3,4-dihydro-3-butyl-3-methyl-1-oxide-2H-pyrrole, 5-amino-3,4-dihydro-3-tert.-butyl-3-methyl-1-oxide-2H-pyrrole, 5-amino-3,4-dihydro-3-sec.-butyl-3-methyl-1-oxide-2H-pyrrole, 5-amino-3,4-dihydro-3-fluoromethyl-3-methyl-1-oxide-2H-pyrrole, 5-amino-3,4-dihydro-3-difluoromethyl-3-methyl-1-oxide-2H-pyrrole, 5-amino-3,4-dihydro-3-trifluoromethyl-3-methyl-1-oxide-2H-pyrrole, 5-amino-3,4-dihydro-3-fluoromethyl-3-ethyl-1-oxide-2H-pyrrole, 5-amino-3,4-dihydro-3-difluoromethyl-3-ethyl-1-oxide-2H-pyrrole, 5-amino-3,4-dihydro-3-trifluoromethyl-3-ethyl-1-oxide-2H-pyrrole, 5-amino-3,4-dihydro-3-fluoromethyl-3-isopropyl-1-oxide-2H-pyrrole, 5-amino-3,4-dihydro-3-difluoromethyl-3-isopropyl-1-oxide-2H-pyrrole, 5-amino-3,4-dihydro-3-trifluoromethyl-3-isopropyl-1-oxide-2H-pyrrole, 5-amino-3,4-dihydro-3-fluoromethyl-3-tert.-butyl-1-oxide-2H-pyrrole, 5-amino-3,4-dihydro-3-difluoromethyl-3-tert.-butyl-1-oxide-2H-pyrrole, 5-amino-3,4-dihydro-3-trifluoromethyl-3-tert.-butyl-1-oxide-2H-pyrrole, 5-amino-3,4-dihydro-3-fluoromethyl-3-sec.-butyl-1-oxide-2H-pyrrole, 5-amino-3,4-dihydro-3-difluoromethyl-3-sec.-butyl-1-oxide-2H-pyrrole, 5-amino-3,4-dihydro-3-trifluoromethyl-3-sec.-butyl-1-oxide-2H-pyrrole, 5-amino-3,4-dihydro-3,3-ethylene-1-oxide-2H-pyrrole, 5-amino-3,4-dihydro-3,3-tetramethylene-1-oxide-2H-pyrrole, 5-amino-3,4-dihydro-3,3-pentamethylene-1-oxide-2H-pyrrole, 5-amino-3,4-dihydro-3,3-hexamethylene-1-oxide-2H-pyrrole, 5-amino-3,4-dihydro-3,3-octamethylene-1-oxide-2H-pyrrole, and the like.

The aminodihydropyrrole (1) can be effectively obtained by reducing the oxidepyrrole (2) with hydrogen in the presence of a catalyst.

Examples of the catalyst to be used are metal catalysts, for example, platinum catalysts such as Pt/C, palladium catalysts such as Pd/C, Raney nickel catalysts, Raney cobalt catalysts, and the like.

An amount of the catalyst is, per one part by weight of the oxidepyrrole (1), usually from 0.00001 to 0.1 part by weight of the platinum catalyst or the palladium catalyst, or 0.01 to 5 parts by weight of the Raney nickel or cobalt catalyst containing about 50% of water.

Usually, the above reduction reaction is carried out under pressure of hydrogen. A pressure is generally from 1 to 50 kg/cm$^2$, preferably from 5 to 30 kg/cm$^2$.

The reduction reaction is usually carried out in the presence of a solvent. Examples of the solvent are alcohols (e.g. methanol, ethanol, isopropanol, etc.), aromatic hydrocarbons (e.g. toluene, etc.), esters (e.g. ethyl acetate, etc.), organic acids which can be used as the solvent (e.g. acetic acid, etc.), and the like.

These solvents may be used independently or as a mixture of two or more of them.

An amount of the solvent is usually from 2 to 500 parts by weight per one part by weight of the oxidepyrrole (2).

Preferably, an organic acid is added to the reduction reaction system. Examples of the organic acid are carboxylic acids (e.g. formic acid, acetic acid, propionic acid, etc.), sulfonic acids (e.g. methanesulfonic acid, p-toluenesulfonic acid, etc.) and so on. These organic acids may be used independently or as a mixture of two or more of them.

The liquid organic acid may be used as a solvent.

When the organic acid is used, its amount is usually from 0.1 to 100 moles per one mole of the oxidepyrrole (2).

In the above reduction reaction, a reaction temperature is usually from 50° to 150° C. A reaction time is usually from 1 to 10 hours.

After the reaction, the formed 5-aminodihydropyrrole (1) can be isolated by, for example, removing the catalyst by filtration and evaporating the solvent off. If necessary, the isolated product may be purified by a conventional purification method such as recrystallization.

Examples of the 5-aminodihydropyrrole (1) are 5-amino-3,4-dihydro-2H-pyrrole, 5-amino-3,4-dihydro-3,3-dimethyl-2H-pyrrole, 5-amino-3,4-dihydro-3,3-diethyl-2H-pyrrole, 5-amino-3,4-dihydro-3,3-dipropyl-2H-pyrrole, 5-amino-3,4-dihydro-3,3-bis-(fluoromethyl)-2H-pyrrole, 5-amino-3,4-dihydro-3,3-bis(difluoromethyl)-2H-pyrrole, 5-amino-3,4-dihydro-3,3-bis(trifluoromethyl)-2H-pyrrole, 5-amino-3,4-dihydro-3,3-bis(pentafluoroethyl)-2H-pyrrole, 5-amino-3,4-dihydro-3-methyl-2H-pyrrole, 5-amino-3,4-dihydro-3-ethyl-2H-pyrrole, 5-amino-3,4-dihydro-3-propyl-2H-pyrrole, 5-amino-3,4-dihydro-3-isopropyl-2H-pyrrole, 5-amino-3,4-dihydro-3-butyl-2H-pyrrole, 5-amino-3,4-dihydro-3-tert.-butyl-2H-pyrrole, 5-amino-3,4-dihydro-3-sec.-butyl-2H-pyrrole, 5-amino-3,4-dihydro-3-fluoromethyl-2H-pyrrole, 5-amino-3,4-dihydro-3-difluoromethyl-2H-pyrrole, 5-amino-3,4-dihydro-3-trifluoromethyl-2H-pyrrole, 5-amino-3,4-dihydro-3-pentafluoroethyl-2H-pyrrole, 5-amino-3,4-dihydro-3-ethyl-3-methyl-2H-pyrrole, 5-amino-3,4-dihydro-3-isopropyl-3-methyl-2H-pyrrole, 5-amino-3,4-dihydro-3-butyl-3-methyl-2H-pyrrole, 5-amino-3,4-dihydro-3-tert.-butyl-3-methyl-2H-pyrrole, 5-amino-3,4-dihydro-3-sec.-butyl-3-methyl-2H-pyrrole, 5-amino-3,4-dihydro-3-fluoromethyl-3-methyl-2H-pyrrole, 5-amino-3,4-dihydro-3-difluoromethyl-3-methyl-2H-pyrrole, 5-amino-3,4-dihydro-3-trifluoromethyl-3-methyl-2H-pyrrole, 5-amino-3,4-dihydro-3-fluoromethyl-3-ethyl-2H-pyrrole, 5-amino-3,4-dihydro-3-difluoromethyl-3-ethyl-2H-pyrrole, 5-amino-3,4-dihydro-3-trifluoromethyl-3-ethyl-2H-pyrrole, 5-amino-3,4-dihydro-3-fluoromethyl-3-isopropyl-2H-pyrrole, 5-amino-3,4-dihydro-3-difluoromethyl-3-isopropyl-2H-pyrrole, 5-amino-3,4-dihydro-3-trifluoromethyl-3-isopropyl-2H-pyrrole, 5-amino-3,4-dihydro-3-fluoromethyl-3-tert.-butyl-2H-pyrrole, 5-amino-3,4-dihydro-3-difluoromethyl-3-tert.-butyl-2H-pyrrole, 5-amino-3,4-dihydro-3-trifluoromethyl-3-tert.-butyl-2H-pyrrole, 5-amino-3,4-dihydro-3-fluoromethyl-3-sec.-butyl-2H-pyrrole, 5-amino-3,4-dihydro-3-difluoromethyl-3-sec.-butyl-2H-pyrrole, 5-amino-3,4-dihydro-3-trifluoromethyl-3-sec.-butyl-2H-pyrrole, 5-amino-3,4-dihydro-3,3-ethylene-2H-pyrrole, 5-amino-3,4-dihydro-3,3-tetramethylene-2H-pyrrole, 5-amino-3,4-dihydro-3,3-pentamethylene-2H-pyrrole, 5-amino-3,4-dihydro-3,3-hexamethylene-2H-pyrrole, 5-amino-3,4-dihydro-3,3-octamethylene-2H-pyrrole, and the like.

The oxidepyrrole (2) may be effectively obtained by reducing the 4-nitrobutanenitrile of the formula (3) with hydrogen the presence of a catalyst.

Examples of the 4-nitrobutanenitrile (3) are 4-nitrobutanenitrile, 3,3-dimethyl-4-nitrobutanenitrile, 3,3-diethyl-4-nitrobutanenitrile, 3,3-dipropyl-4-nitrobutanenitrile, 3,3-bis-(fluoromethyl)-4-nitrobutanenitrile, 3,3-bis(difluoromethyl)-4-nitrobutanenitrile, 3,3-bis(trifluoromethyl)-4-nitrobutanenitrile, 3,3-bis(pentafluoroethyl)-4-nitrobutanenitrile, 3-methyl-4-nitrobutanenitrile, 3-ethyl-4-nitrobutanenitrile, 3-propyl-4-nitrobutanenitrile, 3-isopropyl-4-nitrobutanenitrile, 3-butyl-4-nitrobutanenitrile, 3-tert.-butyl-4-nitrobutanenitrile, 3-sec.-butyl-4-nitrobutanenitrile, 3-fluoromethyl-4-nitrobutanenitrile, 3-difluoromethyl-4-nitrobutanenitrile, 3-trifluoromethyl-4-nitrobutanenitrile, 3-pentafluoroethyl-4-nitrobutanenitrile, 3-ethyl-3-methyl-4-nitrobutanenitrile, 3-isopropyl-3-methyl-4-nitrobutanenitrile, 3-tert.-butyl-3-methyl-4-nitrobutanenitrile, 3-sec.-butyl-3-methyl-4-nitrobutanenitrile, 3-fluoromethyl-3-methyl-4-nitrobutanenitrile, 3-difluoromethyl-3-methyl-4-nitrobutanenitrile, 3-trifluoromethyl-3-methyl-4-nitrobutanenitrile, 3-fluoromethyl-3-ethyl-4-nitrobutanenitrile, 3-difluoromethyl-3-ethyl-4-nitrobutanenitrile, 3-trifluoromethyl-3-ethyl-4-nitrobutanenitrile, 3-fluoromethyl-3-isopropyl-4-nitrobutanenitrile, 3-difluoromethyl-3-isopropyl-4-nitrobutanenitrile, 3-trifluoromethyl-3-isopropyl-4-nitrobutanenitrile, 3-fluoromethyl-3-tert.-butyl-4-nitrobutanenitrile, 3-difluoromethyl-3-tert.-butyl-4-nitrobutanenitrile, 3-trifluoromethyl-3-tert.-butyl-4-nitrobutanenitrile, 3-fluoromethyl-3-sec.-butyl-4-nitrobutanenitrile, 3-difluoromethyl-3-sec.-butyl-4-nitrobutanenitrile, 3-trifluoromethyl-3-sec.-butyl-4-nitrobutanenitrile, 1-cyanomethyl-1-nitromethylcyclopropane, 1-cyanomethyl-1-nitromethylcyclopentane, 1-cyanomethyl-1-nitromethylcyclohexane, 1-cyanomethyl-1-nitromethylcycloheptane, 1-cyanomethyl-1-nitromethylcyclooctane, and the like.

Examples of the catalyst to be used in the reduction of the 4-nitrobutanenitrile (3) are metal catalysts, for example, platinum catalysts such as Pt/C, palladium catalysts such as Pd/C, Raney nickel catalysts, Raney cobalt catalysts, and the like.

An amount of the catalyst is, per one part by weight of the 4-nitrobutanenitrile (3), usually from 0.00001 to 0.1 part by weight of the platinum catalyst or the palladium catalyst, or 0.01 to 5 parts by weight of the Raney nickel or cobalt catalyst containing about 50% of water.

Usually, this reduction reaction is carried out under pressure of hydrogen. A pressure is generally from 1 to 50 kg/cm$^2$, preferably from 5 to 30 kg/cm$^2$.

The reduction reaction is usually carried out in the presence of a solvent. Examples of the solvent are alcohols (e.g. methanol, ethanol, isopropanol, etc.), aromatic hydrocarbons (e.g. toluene, etc.), esters (e.g. ethyl acetate, etc.), organic acids which can be used as the solvent (e.g. acetic acid, etc.), and the like.

These solvents may be used independently or as a mixture of two or more of them.

An amount of the solvent is usually from 2 to 500 parts by weight per one part by weight of the 4-nitrobutanenitrile (3).

In this reduction reaction, a reaction temperature is usually from 50° to 150° C.

When about two equivalents of hydrogen based on the 4-nitrobutanenitrile (3) is consumed, an absorption rate of hydrogen decreases. This point can be regarded as termination of the reduction reaction. The reaction time is usually from 1 to 10 hours.

After the reaction, the formed 2-oxidepyrrole (2) can be isolated by, for example, removing the catalyst by filtration and evaporating off the solvent. If necessary, the isolated product may be purified by a conventional purification method such as recrystallization.

Alternatively, after the termination of the reduction of the 4-nitrobutanenitrile (3), the reduction with hydrogen can be continued further to obtain the 5-aminodihydropyrrole (1) without isolating the oxidepyrrole (2). In this case, it is not necessary to newly add the catalyst or the solvent. In this continuous reduction mode, the amounts and kinds of the solvent and the catalyst may be the same as those in the reduction reaction of the 4-nitrobutanenitrile (3) to the oxidepyrrole (2).

When the 5-aminodihydropyrrole (1) is prepared from the 4-nitrobutanenitrile (3) without isolating the intermediately formed oxidepyrrole (2), the organic acid is preferably added to the reaction system. The kind and amount of the organic acid are the same as those in the reduction reaction of the oxidepyrrole (2) to the 5-aminodihydropyrrole (1). The reaction temperature is usually from 50° to 150° C.

The 4-nitrobutanenitrile (3) may be prepared by reacting the alkenylnitrile of the formula (4) or (4') with nitromethane in the presence of the base.

Examples of the $C_1$–$C_4$ alkyl group for $R^3$ and $R^4$ are methyl group, an ethyl group, a propyl group, an isopropyl group, a butyl group, a sec.-butyl group, a tert.-butyl group, and the like. Examples of the $C_1$–$C_4$ haloalkyl group for $R^3$ and $R^4$ are a fluoromethyl group, a difluoromethyl group, a trifluoromethyl group, a pentafluoroethyl group, and the like.

Examples of the alkenylnitrile (4) are acrylonitrile, 3,3-dimethylacrylonitrile, 3,3-diethylacrylonitrile, 3,3-dipropylacrylonitrile, 3,3-bis(fluoromethyl)acrylonitrile, 3,3-acrylonitrile, 3,3-bis(trifluoromethyl)acrylonitrile, 3,3-bis(pentafluoroethyl)acrylonitrile, 3-methylacrylonitrile, 3-ethylacrylonitrile, 3-propylacrylonitrile, 3-isopropylacrylonitrile, 3-butylacrylonitrile, 3-tert.-butylacrylonitrile, 3-sec.-butylacrylonitrile, 3-fluoromethylacrylonitrile, 3-difluoromethylacrylonitrile, 3-trifluoromethylacrylonitrile, 3-pentafluoroethylacrylonitrile, 3-ethyl-3-methylacrylonitrile, 3-isopropyl-3-methylacrylonitrile, 3-tert.-butyl-3-methylacrylonitrile, 3-sec.-butyl-3-methylacrylonitrile, 3-fluoromethyl-3-methylacrylonitrile, 3-difluoromethyl-3-methylacrylonitrile, 3-trifluoromethyl-3-methylacrylonitrile, 3-fluoromethyl-3-ethylacrylonitrile, 3-difluoromethyl-3-ethylacrylonitrile, 3-trifluoromethyl-3-ethylacrylonitrile, 3-fluoromethyl-3-isopropylacrylonitrile, 3-difluoromethyl-3-isopropylacrylonitrile, 3-trifluoromethyl-3-isopropylacrylonitrile, 3-fluoromethyl-3-tert.-butylacrylonitrile, 3-difluoromethyl-3-tert.-butylacrylonitrile, 3-trifluoromethyl-3-tert.-butylacrylonitrile, 3-fluoromethyl-3-sec.-butylacrylonitrile, 3-difluoromethyl-3-sec.-butylacrylonitrile, 3-trifluoromethyl-3-sec.-butylacrylonitrile, cyclopropylideneacetonitrile, cyclopentylideneacetonitrile, cyclohexylideneacetonitrile, and the like.

Examples of the alkenylnitrile (4') are 3-butenenitrile, 3-methyl-3-butenenitrile, 3-ethyl-3-butenenitrile, 3-butyl-3-butenenitrile, 3-tert.-butyl-3-butenenitrile, 3-sec.-butyl-3-butenenitrile, 3,4-dimethyl-pentenenitrile, 3,4-dimethyl-3-hexenenitrile, 4-ethyl-3-methyl-3-hexenenitrile, 3-ethyl-4- methyl-3-hexenenitrile, 3,4-diethyl- 3-hexenenitrile, 3-trifluoromethyl-3-butenenitrile, 4-chloromethyl-3-methyl-3-butenenitrile, and the like.

An amount of nitromethane to be used is usually from 1 to 50 parts by weight per one part by weight of the alkenylnitrile (4) or (4').

As the base, an organic base such as 1,8-diazabicyclo[5.4.0]-7-undecene, 1,5-diazabicyclo[4.3.0]-5-nonene, etc. is used.

An amount of the base is usually from 0.01 to 2 moles per one mole of the alkenylnitrile (4) or (4').

In this reaction, an organic solvent may be used. Examples of the optionally used solvent are water-insoluble solvents (e.g. toluene, xylene, monochlorobenzene, dichlorobenzene etc.), water-soluble solvents (e.g. methanol, ethanol, tert.-butanol, dioxane, etc.), and the like.

An amount of the solvent is usually from 1 to 50 parts by weight per one part weight of the alkenylnitrile (4) or (4').

A reaction temperature is usually from 0° to 140° C., and a reaction time is usually from 1 to 20 hours.

After the reaction, the formed 4-nitrobutanenitrile (3) may be isolated by, for example, adding the organic solvent and an acidic water to the reaction mixture to extract the 4-nitrobutanenitrile (3) in the organic solvent and evaporating the solvent off. If necessary, the 4-nitrobutanenitrile (3) may be purified by a conventional method such as column chromatography.

The oxidepyrrole (2) of the present invention is useful as an intermediate of the 5-aminodihydropyrrole (1) which is an important raw material of various agrochemicals such as herbicides. According to the present invention, the 5-aminodihydropyrrole (1) can be easily prepared from the oxidepyrrole (2) advantageously in the industrial scale.

PREFERRED EMBODIMENTS OF THE INVENTION

The present invention will be illustrated by the following Examples, which do not limit the scope of the present invention in any way.

EXAMPLE 1

1-(1): Preparation of 3,3-dimethyl-4-nitrobutanenitrile

In a one liter glass reactor equipped with a thermometer, a cooling apparatus and a stirrer, 3-methyl-3-butenenitrile (37.0 g, 0.456 mol) and nitromethane (557.0 g, 9.125 mol) were charged. Then, 1,8-diazabicyclo[5.4.0]-7-undecene (13.9 g, 0.091 mol) was dropwise added over a period of 5 minutes at room temperature while stirring. After the dropwise addition, the mixture was heated and refluxed at 103° C. for 13.5 hours. After cooling the mixture to room temperature, unreacted nitromethane was evaporated off under reduced pressure. To the residue, dichloromethane (300 g) and 5% sulfuric acid (300 g) were added and stirred. Thereafter, the mixture was phase separated to obtain a dichloromethane layer. To the aqueous layer, dichloromethane (300 g) was added and the mixture was phase separated to obtain a dichloromethane layer. Two dichloromethane layers were combined and washed with water (300 g). After drying the dichloromethane solution over anhydrous sodium sulfate, dichloromethane was evaporated off under reduced pressure to obtain brown crystal 3,3-dimethyl-4-nitrobutanenitrile (60.7 g), a purity of which was 92.0%. Its yield was 86.1% based on 3-methyl-3-butenenitrile.

The brown crystal was purified by silica gel column chromatography (hexane: ethyl acetate=9:1 to 3:1) to obtain white crystal 3,3-dimethyl-4-nitrobutanenitrile having a purity of 99.7%.

$^1$H-NMR: δ (ppm) (CDCl$_3$)=1.25 (s, 6H), 2.58 (s, 2H), 4.40 (s, 2H).

GC/MS: M/Z=96 (100), 69 (33), 55 (62).

Melting point: 95°–98° C.

1-(2): Preparation of 5-amino-3,4-dihydro-3,3-dimethyl-1-oxide-2H-pyrrole

In a 300 ml autoclave, brown crystal 3,3-dimethyl-4-nitrobutanenitrile which was obtained in the above step 1-(1) (1.42 g, 9.19 mmol, purity: 92.0%), 5% palladium/carbon (water content of 50%) (0.2 g) and methanol (80 g) were charged and reacted with hydrogen under hydrogen pressure of 12 kg/cm$^2$ at 70° C. for 2 hours and then under hydrogen pressure of 20 kg/cm$^2$ at 100° C. for 30 minutes. After cooling to room temperature, the catalyst was filtrated off, and from the filtrate, methanol was evaporated off to obtain pale yellow crystal (1.22 g). The pale yellow crystal (0.80 g) was washed with dichloromethane (3 g) three times and dried to obtain white crystal 5-amino-3,4-dihydro-3,3-dimethyl-1-oxide-2H-pyrrole (0.55 g). According to the analysis by high performance liquid chromatography (UV 210 nm), a purity of 5-amino-3,4-dihydro-3,3-dimethyl-1-oxide-2H-pyrrole was 98.7%, and its yield was 70.3% based on 3,3-dimethyl-4-nitrobutanenitrile.

$^1$H-NMR: δ (ppm) (CDCl$_3$)=1.19 (s, 6H), 2.52 (s, 2H), 3.47 (s, 2H), 5.00 (bs, 2H).

FD/MS: M/Z=128.

Melting point: 246°–249° C.

1-(3): Preparation of 5-amino-3,4-dihydro-3,3-dimethyl-2H-pyrrole

In a 300 ml autoclave, white crystal 5-amino-3,4-dihydro-3,3-dimethyl-1-oxide-2H-pyrrole obtained in the step of 1-(2) (0.20 g, 1.56 mmol), 5% palladium/carbon (water content of 50 (0.1 g) and methanol (80 g) were charged and reacted with hydrogen under hydrogen pressure of 20 kg/cm$^2$ at 100° C. for 2 hours. After cooling to room temperature, the catalyst was filtrated off, and from the filtrate, methanol was evaporated off to obtain white crystal. According to the analysis by high performance liquid chromatography, a yield of 5-amino-3,4-dihydro-3,3-dimethyl-2H-pyrrole was 83.0% based on 5-amino-3,4-dihydro-3,3-dimethyl-1-oxide-2H-pyrrole. After recrystallization from toluene and drying, white crystal 5-amino-3,4-dihydro-3,3-dimethyl-2H-pyrrole having a purity of 99.0% was obtained.

$^1$H-NMR: δ (ppm) (CDCl$_3$)=1.12 (s, 6H), 2.25 (s, 2H), 3.30 (s, 2H), 4.74 (bs, 1H), 7.30 (s, 1H).

GC/MS: M/Z=112 (48), 97 (31), 56 (100).

Melting point: 118°–122° C.

EXAMPLE 2

In a 300 ml autoclave, brown crystal 3,3-dimethyl-4-nitrobutanenitrile which was obtained in the above step 1-(1) (7.00 g, 0.0453 mol, purity: 92.0%), 5% palladium/carbon (water content of 50%) (1.0 g), methanol (40 g) and acetic acid (50 g) were charged and reacted with hydrogen under hydrogen pressure of 20 kg/cm$^2$ at 100° C. for 4 hours. After cooling to room temperature, the catalyst was filtrated off, and from the filtrate, methanol and acetic acid were evaporated off. The product was analyzed by high performance liquid chromatography to find that a yield of 5-amino-3,4-dihydro-3,3-dimethyl-2H-pyrrole was 90.9% based on 3,3-dimethyl-4-nitrobutanenitrile.

Comparative Example

In a 50 ml glass reactor equipped with a thermometer, a cooling apparatus and a stirrer, 4,4-dimethyl-2-pyrrolidinone (0.50 g, 4,4 mmol) and phosphorus oxychloride (6.7 g, 44.0 mmol) were charged and refluxed for 4 hours. After cooling to room temperature, unreacted phosphorus oxychloride was evaporated off at a temperature of 50° C. or lower under reduced pressure. The concentrated reaction mixture was cooled to 0° C. and 6% ammonia/methanol solution (5.0 g) was dropwise added over a period of 10 minutes while stirring. After stirring at 0° C. for further 30 minutes, the temperature was raised to 70° C., and the mixture was stirred at that temperature for 1.5 hours. A part of the reaction mixture was diluted with dichloromethane, washed with 0.1N aqueous sodium hydroxide solution and analyzed by high performance liquid chromatography to find that no desired 5-amino-3,4-dihydro-3,3-dimethyl-2H-pyrrole was formed.

What is claimed is:

1. A process for preparing a 5-aminodihydropyrrole of the formula (1):

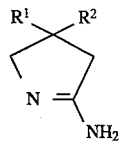

(1)

wherein $R^1$ and $R^2$ are the same or different and represent a hydrogen atom, a lower alkyl group or a lower haloalkyl group, or together form a $C_2$–$C_{10}$ alkylene group which may be substituted with a halogen comprising reducing an oxidepyrrole of the formula (2):

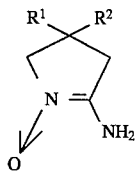

(2)

wherein $R^1$ and $R^2$ are the same as defined above with hydrogen in the presence of a catalyst.

2. The process according to claim 1, wherein said catalyst is a metal catalyst.

3. The process according to claim 2, wherein said metal catalyst is a catalyst selected from the group consisting of a platinum catalyst, a palladium catalyst, a Raney nickel catalyst and a Raney cobalt catalyst.

4. The process according to claim 2, wherein said metal catalyst is a platinum catalyst or a palladium catalyst.

5. The process according to claim 1, wherein $R^1$ and $R^2$ are both lower alkyl groups having 1 to 5 carbon atoms.

6. The process according to claim 1, wherein said oxidepyrrole (2) is prepared by reducing a 4-nitrobutanenitrile of the formula (3):

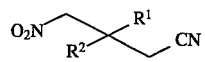

(3)

wherein $R^1$ and $R^2$ are the same as defined above with hydrogen in the presence of a catalyst.

7. The process according to claim 6, wherein said catalyst is a metal catalyst.

8. The process according to claim 7, wherein said metal catalyst is a catalyst selected from the group consisting of a platinum catalyst, a palladium catalyst, a Raney nickel catalyst and a Raney cobalt catalyst.

9. The process according to claim 7, wherein said metal catalyst is a platinum catalyst or a palladium catalyst.

10. The process according to claim 6, wherein the prepared oxidepyrrole (2) is used in the subsequent reduction without isolation.

11. The process according to claim 6, wherein said 4-nitrobutanenitrile (3) is prepared by reacting an alkenylnitrile of the formula (4):

(4)

or the formula (4'):

(4')

wherein $R^1$ and $R^2$ are the same as defined above and $R^3$ and $R^4$ are the same or different and represent a hydrogen atom, a $C_1$–$C_4$ alkyl group or a lower $C_1$–$C_4$ haloalkyl group with nitromethane in the presence of a base.

12. The process according to claim 11, wherein said base is an organic base.

13. The process according to claim 12, wherein said organic base is at least one compound selected from the group consisting of 1,8-diazabicyclo[5.4.0]-7-undecene and 1,5-diazabicyclo[4.3.0]-5-nonene.

14. A process for preparing an oxidepyrrole of the formula (2):

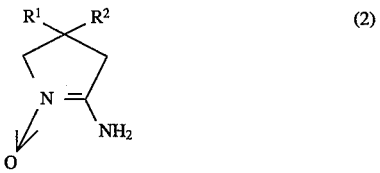

(2)

wherein $R^1$ and $R^2$ are the same or different and represent a hydrogen atom, a lower alkyl group or a lower haloalkyl group, or together form a $C_2$–$C_{10}$ alkylene group which may be substituted with a halogen comprising reducing a 4-nitrobutanenitrile of the formula (3):

(3)

wherein $R^1$ and $R^2$ are the same as defined above with hydrogen in the presence of a catalyst.

15. The process according to claim 14, wherein $R^1$ and $R^2$ are both lower alkyl groups having 1 to 5 carbon atoms.

16. The process according to claim 14, wherein said 4-nitrobutanenitrile (3) is prepared by reacting an alkenylnitrile of the formula (4):

(4)

or the formula (4'):

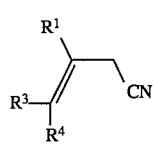
(4')
wherein $R^1$ and $R^2$ are the same as defined above and $R^3$ and $R^4$ are the same or different and represent a hydrogen atom, a $C_1$–$C_4$ alkyl group or a lower $C_1$–$C_4$ haloalkyl group with nitromethane in the presence of a base.
\* \* \* \* \*

UNITED STATES PATENT AND TRADEMARK OFFICE
CERTIFICATE OF CORRECTION

PATENT NO. : 5,498,725
DATED      : March 12, 1996
INVENTOR(S): Mitsuhiro Matsumoto and Kunihiko Fujita It is certified that error appears in the above-indentified patent and that said Letters Patent is hereby corrected as shown below:

On The Title Page,

Item [75], change "Misuhiro Matsumoto" to read --Mitsuhiro Matsumoto--.

Signed and Sealed this

Eighth Day of October, 1996

Attest:

BRUCE LEHMAN

Attesting Officer

Commissioner of Patents and Trademarks